(12) United States Patent
Wright et al.

(10) Patent No.: US 7,914,490 B2
(45) Date of Patent: Mar. 29, 2011

(54) AMBULATORY INFUSION PUMP ASSEMBLY AND HOUSING THEREFOR

(75) Inventors: David W. Wright, Littleton, CO (US); Constance Ann Gorden, Castle Rock, CO (US); Christopher Andrews, Fort Collins, CO (US)

(73) Assignee: WalkMed Infusion LLC, Englewood, CO (US)

( * ) Notice: Subject to any disclaimer, the term of this patent is extended or adjusted under 35 U.S.C. 154(b) by 0 days.

(21) Appl. No.: 12/607,495

(22) Filed: Oct. 28, 2009

(65) Prior Publication Data

US 2010/0106091 A1    Apr. 29, 2010

Related U.S. Application Data

(60) Provisional application No. 61/109,217, filed on Oct. 29, 2008.

(51) Int. Cl.
*A61M 1/00* (2006.01)
(52) U.S. Cl. ...................................... 604/151; 417/477.2
(58) Field of Classification Search .............. 604/65–67, 604/118–121, 131–147, 151–155, 890.1–892.1; 417/477.2
See application file for complete search history.

(56) References Cited

U.S. PATENT DOCUMENTS

| | | | | |
|---|---|---|---|---|
| 5,298,025 A | * | 3/1994 | Hessel et al. | 604/118 |
| 5,634,896 A | * | 6/1997 | Bryant et al. | 604/29 |
| 5,938,640 A | * | 8/1999 | Maget et al. | 604/145 |
| 2001/0039397 A1 | * | 11/2001 | Kriesell et al. | 604/132 |
| 2003/0138334 A1 | * | 7/2003 | Vandlik et al. | 417/477.2 |
| 2004/0064097 A1 | * | 4/2004 | Peterson | 604/132 |
| 2005/0095153 A1 | * | 5/2005 | Demers et al. | 417/477.2 |
| 2009/0009179 A1 | * | 1/2009 | Sobue et al. | 324/519 |

* cited by examiner

*Primary Examiner* — Nicholas D Lucchesi
*Assistant Examiner* — Gerald Landry, II

(57) ABSTRACT

An ambulatory infusion pump assembly and housing therefore has a cover and a base providing an enclosed cavity. The system includes a liquid pump in fluid communication with a supply source of a liquid drug. The pump and supply source are received in the housing cavity. Further, the system includes a seal providing a liquid tight seal between the cover and the base. A through passage extends from the enclosed cavity external to the housing and an infusion tube extends through the through passage. A fluid tight seal is formed about the infusion tube. A vent is provided in the housing that maintains a balanced pressure state between the enclosed cavity and the atmosphere, while at the same time, the vent prevents the ingress and egress of contaminants into and fluid out of the enclosed cavity.

25 Claims, 6 Drawing Sheets

AMBULATORY INFUSION PUMP ASSEMBLY AND HOUSING THEREFOR

CROSS-REFERENCE TO RELATED APPLICATION

This application claims the benefit of U.S. Provisional Application Ser. No. 61/109,217, filed Oct. 29, 2008, which is incorporated herein by reference in its entirety.

BACKGROUND OF THE INVENTION

1. Technical Field

This invention relates generally to infusion pump systems, and more particularly to ambulatory infusion pump systems having pump enclosures.

2. Related Art

Ambulatory infusion pumps for infusing a prescribed dosage of medication are worn by patients for days or weeks on end. During this time, patients are restricted from taking baths and showers, and generally, from participating in events that would expose the pump to contamination, such as water, for example. As such, to avoid contamination from reaching the pump, patients often wrap their pump in a plastic bag.

Aside from the need to prevent contamination from reaching the pump, recent healthcare regulations are being considered that would help to shield healthcare workers, nurses, doctors and other healthcare providers from being exposed to certain chemicals and drugs. Some of these drugs are administered by the aforementioned ambulatory infusion pumps. One such regulation is the USP Chapter 797, which limits the exposure of drugs deemed potentially harmful during compounding. Accordingly, given these regulations and efforts to prevent the potential exposure to drugs identified as being potentially harmful, it is believed increasingly important to prevent the potential for drugs from inadvertently leaking from an ambulatory pump system.

SUMMARY OF THE INVENTION

An ambulatory infusion pump assembly includes a housing having a cover and a base forming an internal cavity. A fluid pump is received in the cavity in fluid communication with a supply source of liquid drug within the cavity. A tube extends from the pump to an environment external to the cavity. A seal is sandwiched between the cover and the base to form a liquid tight seal between the cover and the base. A vent is provided in the housing to maintain an equalized pressure between the cavity and the environment, while at the same time inhibiting the passage of liquid between the cavity and the environment.

In accordance with another aspect of the invention, the vent is hydrophobic.

In accordance with another aspect of the invention, the through passage extends through the seal.

In accordance with another aspect of the invention, at least one of the cover and/or base has resilient interface buttons attached thereto in sealed configuration with the buttons being configured to interact with sensors on the pump.

In accordance with another aspect of the invention, the cover and base are configured to be opened relative to one another to allow ready access to the cavity within the housing and closed, whereupon the liquid tight seal is established between the cover and base.

In accordance with another aspect of the invention, an ambulatory infusion pump housing is provided. The housing includes a cover and a base configured to mate with the cover to provide an enclosed internal cavity. A seal is sandwiched between the cover and the base. The seal protects the cavity against ingress of contamination therein and egress of liquid therefrom. A vent is provided in at least one of the cover and/or the base. The vent maintains a substantially equalized pressure between the cavity and an environment external to the cavity and substantially prevents the passage of liquid between the cavity and the environment therethrough. Accordingly, the contents within the enclosed cavity are protected against contamination external to the enclosed cavity, while at the same time, liquid is prevented from leaking inadvertently from the enclosed cavity.

BRIEF DESCRIPTION OF THE DRAWINGS

These and other aspects, features and advantages of the invention will become more readily appreciated when considered in connection with the following detailed description of presently preferred embodiments and best mode, appended claims and accompanying drawings, in which:

DETAILED DESCRIPTION OF PRESENTLY PREFERRED EMBODIMENTS

Figure 1:
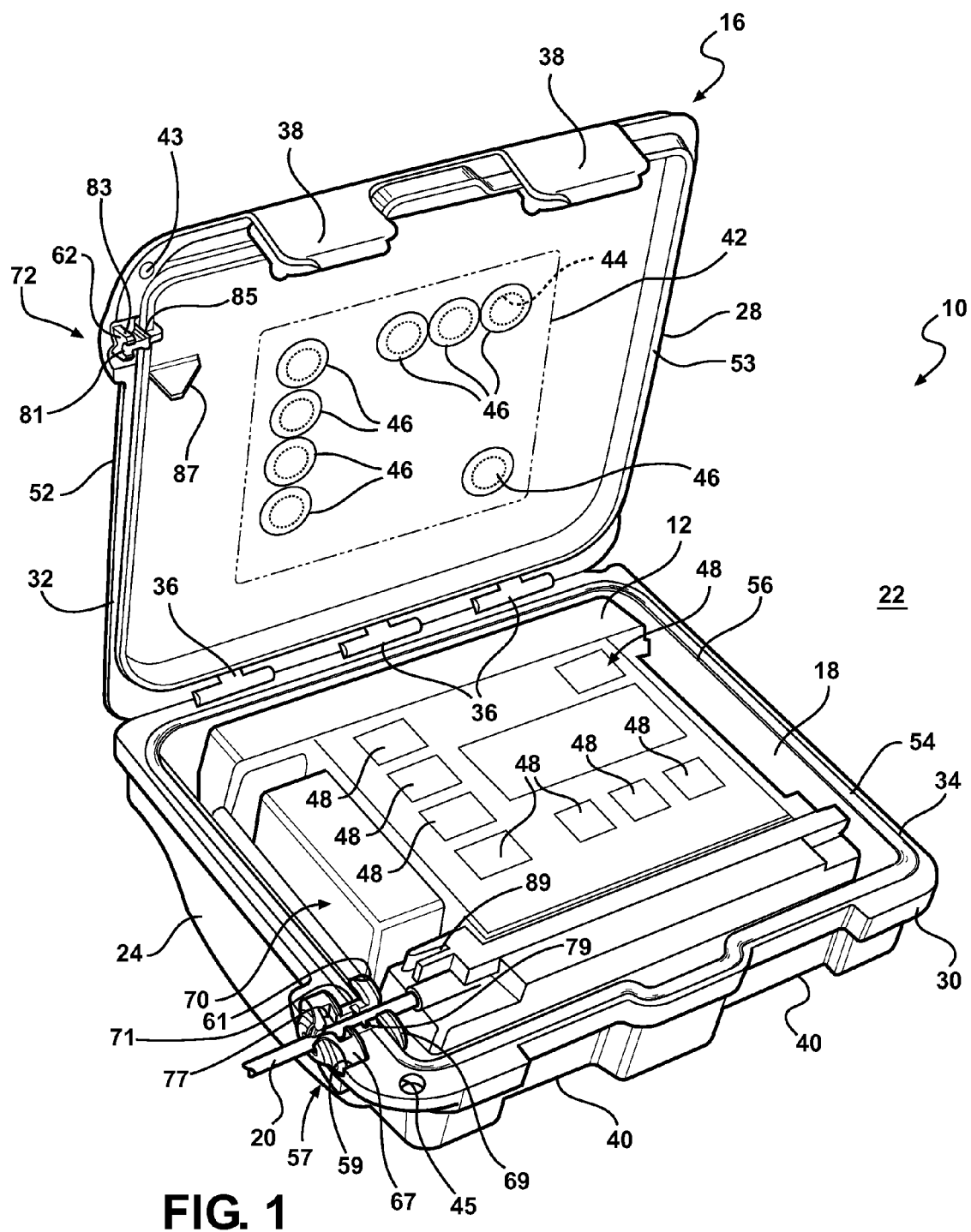
FIG. 1 is a top perspective view of an ambulatory infusion pump system constructed in accordance with one presently preferred embodiment of the invention shown in an open configuration.

Referring in more detail to the drawings, FIG. 1 illustrates an ambulatory infusion pump system, also referred to as assembly 10, in accordance with one presently preferred aspect of the invention. The assembly 10 includes a liquid infusion pump, referred to hereafter as pump 12, a supply source 14 (FIG. 5) containing a liquid drug, such as a pliable pouch, bag or other type of pliable container having a liquid drug treatment in fluid communication with the pump 12, a case, also referred to as housing 16, providing an enclosed internal cavity 18 sized for receipt of the pump 12 and the supply source 14, and a tube 20 operably attached to the pump 12 to provide a flow path of the liquid drug from the supply source 14 to a patient external from the cavity 18. Other than the fluid flow provided through the tube 20, the cavity 18 is completely sealed off from fluid communication with an environment 22 external to the housing 16. Accordingly, any fluid coming into contact with an outer surface 24 of the housing 16 is prevented from entering the cavity 18, and likewise, any fluid within the cavity 18 is prevented from exiting the cavity 18, other than through the tube 20 as intended. Accordingly, the cavity 18 and the contents therein are protected against contamination from elements external to the housing 16, and further, any liquid drug external to the supply source 14 and within the cavity 18 is prevented from inadvertently leaking from the housing 16.

Given the liquid drug is dispensed from the supply source 14 outwardly from the cavity 18, the volume within the supply source 14 and the mass within the cavity 18 decrease as the liquid drug exits the supply source 14 and the cavity 18, respectively. As such, in order to prevent a vacuum pressure from forming in the cavity 18, a pressure equalization vent, referred to hereafter as vent 26, is provided in the housing 16 to enable the pressure within the cavity 18 to be maintained and balanced in equilibrium or substantial equilibrium with the atmospheric pressure of the environment 22 as the liquid drug is dispensed. To prevent liquid from being able to pass through the vent 26, the vent 26 is provided as a hydrophobic vent. Accordingly, the assembly 10 provides a mechanism in which the ingress of contamination, including liquids and other sources of non-liquid contamination, into the cavity 18 is prevented, while also preventing the inadvertent egress of the liquid drug from within the cavity 18 to the environment 22. Further, with the pressure being balanced between the cavity 18 and the environment 22, the pump 12 is able to function as intended.

The housing 16 has a cover 28 and a base 30 with respective peripheries 32, 34 configured for liquid-tight sealed engagement with one another. The cover 28 and base 30 are attached to one another via a hinge, shown here as a plurality of hinges 36 coaxially aligned with one another such that the cover 28 and base 30 provide a clam-shell type enclosure. To facilitate maintaining the cover 28 in locked and sealed engagement with the base 30, a releasable lock mechanism can be provided, such as by a resilient latch or latches 38 on one of the cover or base, and shown here as on the cover 28, for releasable engagement with a corresponding catch or catches 40 on the other of the cover or base, and shown here as on the base 30. Accordingly, the cover 28 can be locked in sealed engagement with the base 30 by fastening the latches 38 to the catches 40, wherein the latches 38 can be selectively released from the catches 40 to open the cover 28 and provide access to the cavity 18, as desired. The latches 38, although shown as a single piece of material with the cover 28, could be formed as a separate piece of material and attached to the cover 28, such as by pivotal hinge connections, for example. To prevent unwanted access to the cavity 18, and thus, to the drug within the cavity 18, other than by a qualified caregiver, the lock mechanism can be provided with a "keyed" mechanism, with "keyed" meaning any suitable lock mechanism that is only accessible by the caregiver, if desired. In addition, the cover 28 and base 30 can be configured for attachment of a supplemental locking device, such as a pad lock or other device, shown here as a tie wrap 41 type device, by way of example and without limitation, wherein the tie wrap 41 is secured through axially aligned openings 43, 45 in the cover 28 and base 30, respectively.

Figure 5:
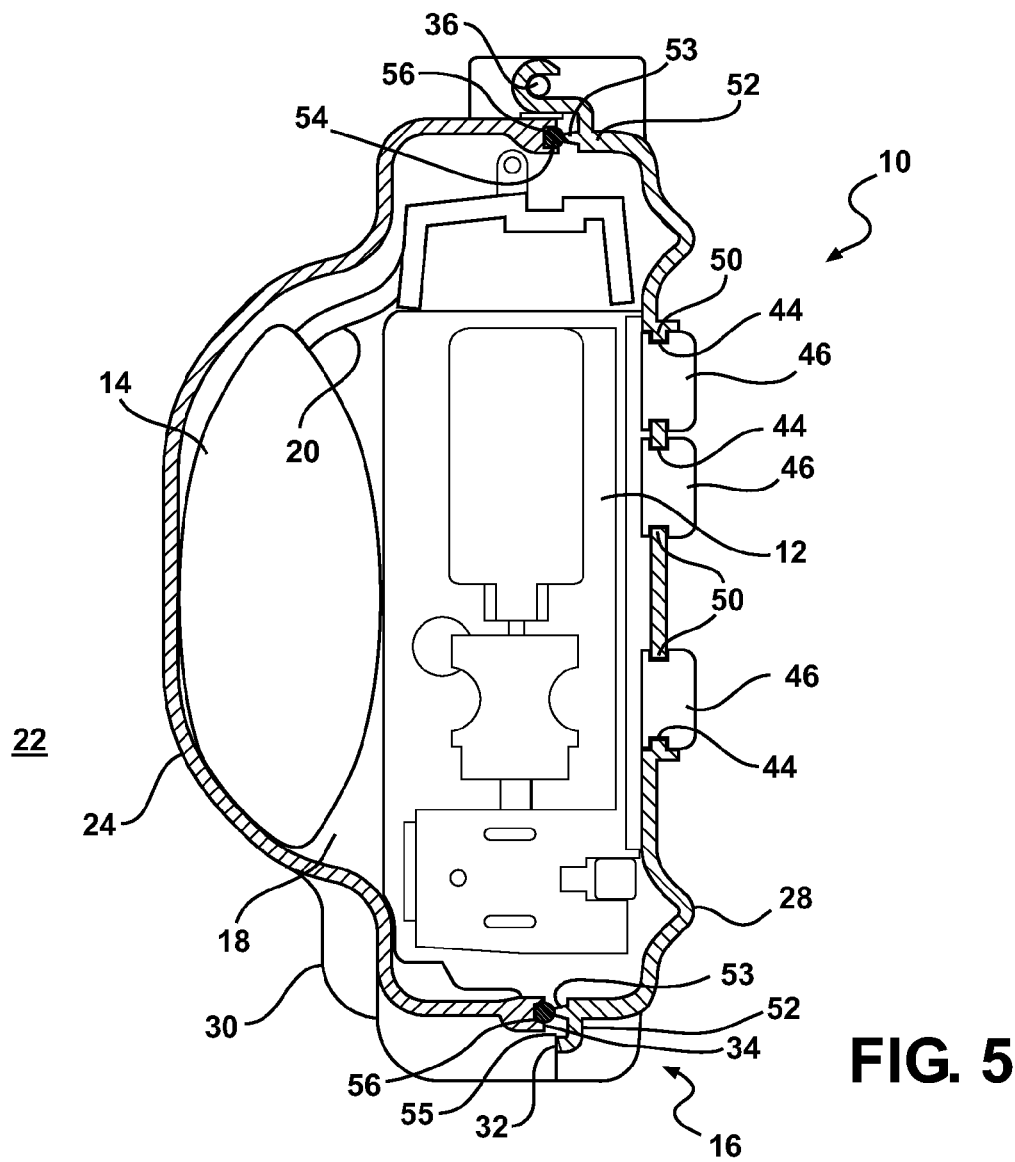
FIG. 5 is a partially cross-sectioned side view of the pump system showing interface buttons disposed in the cover.
Figure 5A:
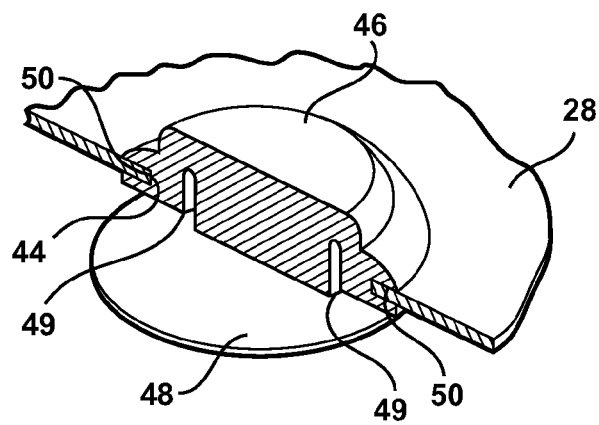
FIG. 5A is an enlarged cross-sectioned perspective view of one of the interface buttons of FIG. 5.

The cover 28 is shown here as having an enclosure display window 42 that allows clear viewing into the cavity 18. The display window 42, aside from providing a clear view of the pump 12 within the cavity 18, provides an ability to interact with the control features on the pump 12 to selectively regulate its function. For example, the display window 42 shown has a plurality of openings 44, sized for liquid tight, sealed receipt of interface control buttons, referred to hereafter as buttons 46. The buttons 46 are preferably able to flex inwardly and outwardly in a resilient manner so that upon pressing on an outer upper face of the respective button, an inner underside of the button 46 springs inwardly into engagement with a corresponding interface member, such as a switch or sensor 48, on the pump 12 to actuate or deactivate the intended function of the pump 12, as desired. Upon releasing applied pressure from the button 46, the button 46 automatically returns to its unflexed, unbiased state. To facilitate the spring-like flexure of the buttons 46, the buttons 46 can be provided with an annular, recessed groove 49 (FIG. 5A) extending into the underside of the button. As shown in FIG. 5, to facilitate forming the fluid-tight seal, the buttons 46 can be attached within the openings 44 via a line-to-line or slight interference fit, with a periphery of the cover 28 being received in an annular recess 50 of the button 46. With the buttons 46 being press-fit within the openings 44, the buttons 46 can be readily removed and replaced, such as when worn, for example. Of course, in addition to being press-fit, the buttons 46 can be permanently attached to the cover 28 in a variety of ways, such as being injection or insert molded thereto, or via an adhesive or weld joint, for example.

To facilitate forming the liquid tight seal between the cover 28 and the base 30, the cover 28 has a peripherally extending elastomeric seal and/or a peripherally extending sealing flange 52. The flange 52 is formed extending continuously or substantially continuously about the entire periphery of the cover 28 for operable, sealed abutment with a peripherally extending seal 54. The flange 52 is shown here as having a sealing surface, represented here as an annular projection, also referred to as rib 53, depending from a substantially planar surface of the flange 52, wherein the rib 53 is configured to sealingly abut an upper surface of the seal 54.

Figure 3:
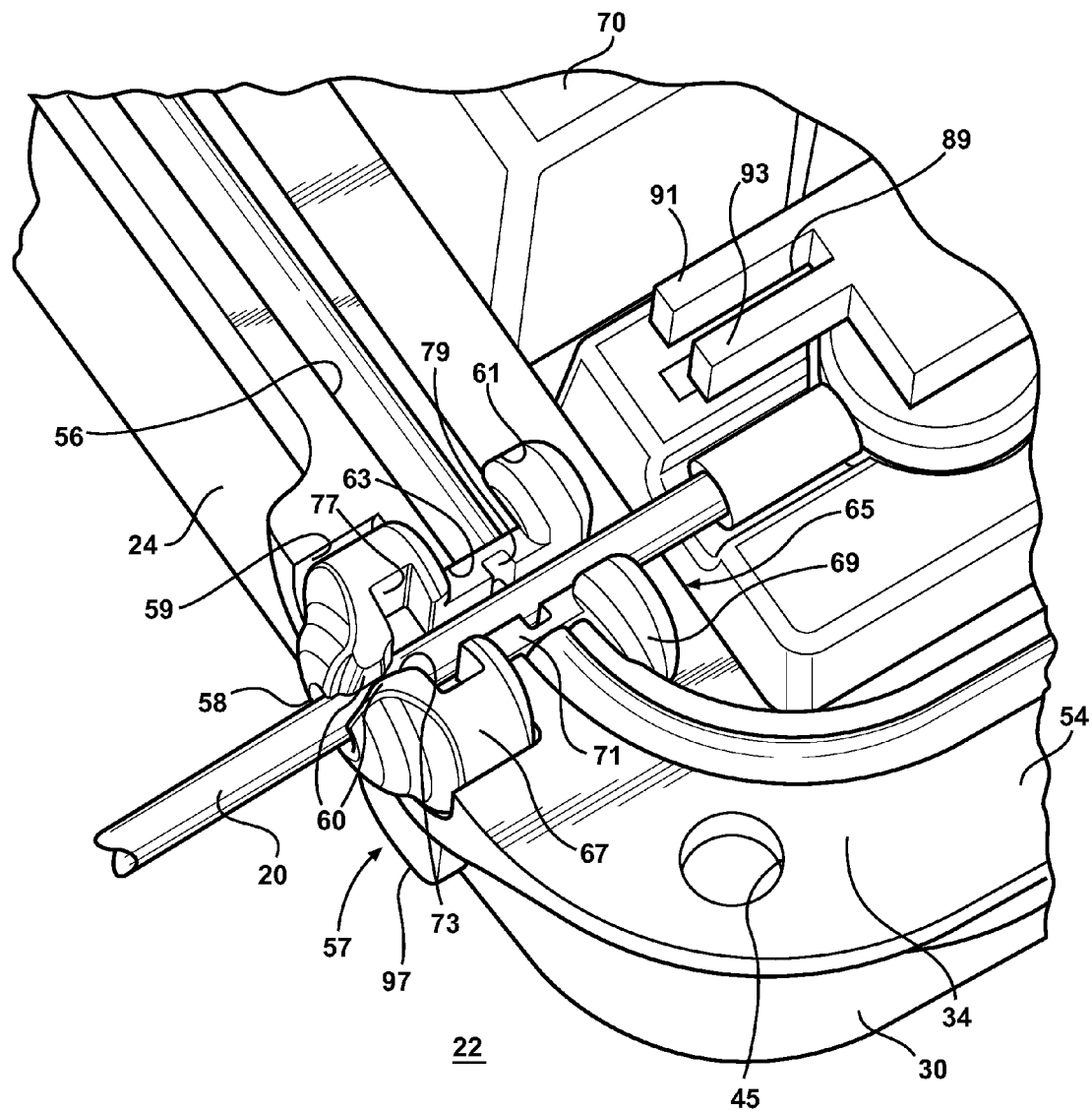
FIG. 3 is a partial perspective view of the pump system of FIG. 1 showing a sealed liquid flow passage extending between an interior cavity and exterior of the pump system with a cover being opened from a base of the pump system.

The seal 54 is represented here, by way of example and without limitation, as being received in a channel 56 extending about the periphery 34 of the base 30. It should be recognized that the seal 54 could be otherwise attached to the upper periphery 34 of the base 30 other than by being received in the channel 56, such as by being adhered to the periphery 34 and/or by having a recessed slot configured in the seal 54 for receipt of a peripherally extending flange or tongue (not shown) on the periphery 34 of the base 30, for example. To ensure a complete liquid tight seal is established between the cover 28 and the base 30, the channel 56, conforms in shape and is configured to ensure that the seal 54 received therein is always in direct, sealed engagement with the seal surface 53 of the cover 28 upon fully closing the cover 28. The channel 56 is represented as having semi-annular recess 57 to receive and conform with a portion of the seal 54. As best shown in FIG. 3, the recess 57, by way of example, is shown having a semi-annular, dumbbell configuration, thereby having laterally spaced recessed regions 59, 61 (laterally spaced meaning one region is proximate the outer surface 24 and the other region is proximate the cavity 18) interconnected by a recessed, necked down channel 63. The differently configured regions 59, 61, 63 are shaped to conform or substantially conform with the an annular, generally dumbbell shaped portion 65 of the seal 54.

The dumbbell shaped portion 65 has an annulus 67 configured for sealed receipt in the recessed region 59 and an annulus 69 configured for sealed receipt in the recessed region 61 with a reduced diameter or necked down portion 71 extending between the annulus 67, 69 and being configured for sealed receipt in the necked down channel 63. To facilitate receiving and providing a continuous, fluid tight seal about the tube 20 extending from within the cavity 18 to the environment 22, the dumbbell shaped, or toroidal portion 65 of the seal 54, as best shown in FIG. 3, has an elongate opening, also referred to as a channel 58, extending across its length, wherein the length extends between the annulus 67, 69 across the necked down portion 71. The portion of the channel 58 receiving the tube 20, to facilitate assembly, can be formed having a slit shown generally at 73 forming the seal having generally C-shape or broken O-shape, thereby providing the channel 58 with a circumferentially discontinuous wall having overhanging lips 60 that completely or substantially overlie and encircle the tube 20 upon the tube 20 being fully disposed in the channel 58. Accordingly, upon disposing the tube 20 in the channel 58, the tube 20 is completely or substantially encircled in sealed abutment with the dumbbell shaped portion 65 of the seal 54 about its full circumference to ensure a liquid tight seal is established about the tube 20 upon closing the cover 28. Further, to facilitate assembly of the tube 20 into the channel 58, discussed further below, the dumbbell shaped portion 65 has a first pocket 77, shown here, by way of example, extending into the annulus 67 through to the channel 58 and a second pocket 79, shown here, by way of example, extending into the necked down portion 71 through to the channel 58.

Figure 4:
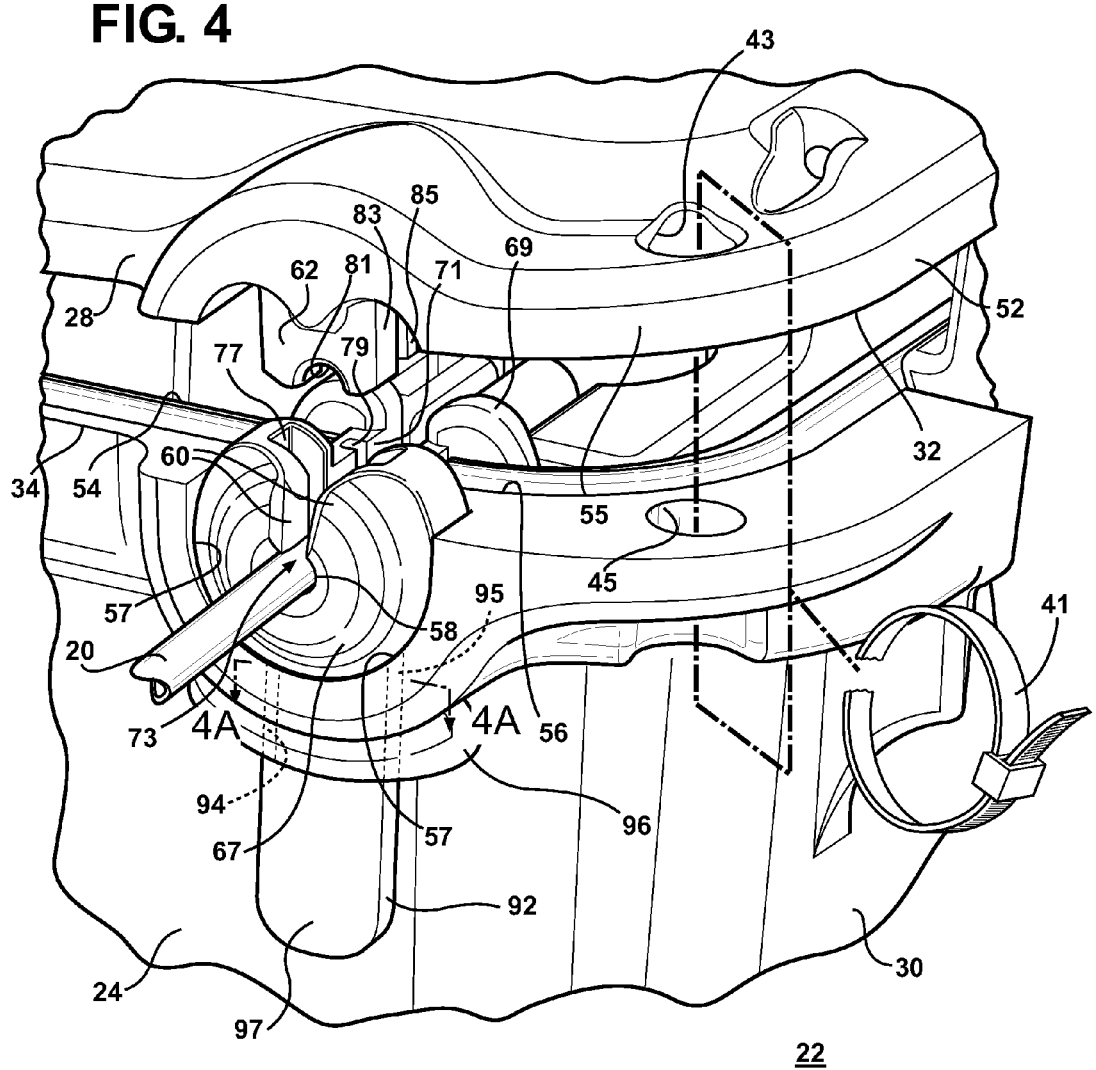
FIG. 4 is a partial perspective view of the sealed liquid flow passage with the cover being partially closed on the base.

To ensure the tube 20 is received completely in the channel 58, the flange 52 on the cover 28 has a projection 62 configured to urge the tube 20 into full, sealed receipt in the channel 58 upon closing the cover 28. As best shown in FIGS. 1 and 4, the projection 62 has a contoured, elongate concave surface 81 configured to conform with the convex outer surface of the tube 20. As such, while closing the cover 28, the concave surface 81 engages the tube 20 and pushes the tube 20 downwardly through the slit 73 beneath the lips 60 and into the pocket 58, if not already fully received therein. The projection 62 also has a pair of laterally spaced tongues 83, 85 sized for close receipt in the pockets 77, 79, respectively. Accordingly, while closing the cover 28, the projection 62 is assured of being guided into its proper orientation within the dumbbell shaped portion 65, thereby assuring the tube 20 is properly urged into the channel 58. To further assure the cover 28 is guided properly while being closed, a tab 87 depends from the cover 28 for close receipt within a slot 89 provided by a pair of fingers 91, 93 spaced from one another. Accordingly, multiple assurances are provided to ensure the cover 28 is closed properly on the base 30, thereby providing added assurance that the tube 20 is properly received and sealed in the channel 58. It should be recognized that the dumbbell shaped portion 65 of the seal 54 can be formed as a single piece of material with the seal 54, or it can be formed as a separate piece of material, thereby provided the seal 54 having a first piece of material extending substantially about the periphery of the housing 16 and a second piece of material separate from the first piece of material providing the fluid-tight seal about the tube 20. Further, the dumbbell shaped portion 65 can be provided having a continuous, unbroken wall, thereby not having the slit 73, such as a generally circular grommet, for example.

Figure 4A:
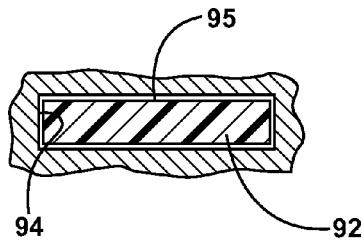
FIG. 4A is a partial cross-sectional view of the base showing a through opening with a portion of a seal extending therethrough.

As best shown in FIGS. 4 and 4A, to facilitate attaching the dumbbell shaped portion 65 to the base 30, aside from using an adhesive, for example, an interference fit can be provided between a retaining tab 92 of the dumbbell shaped portion 65 and the periphery 34 of the base 30. The periphery 34 is provided with a through opening 94 extending from the semi-annular recess 57 downwardly and exiting the periphery 34. The retaining tab 92 has a midsection 95 that is received in a close fit through the through opening 94 and an enlarged retaining head 96. The retaining head 96, being constructed of an elastomeric material, can be pulled via a pull tab 97 forcefully to elastically deform through the opening 94, and then, when pulled sufficiently to exit the opening 94, the head 96 expands elastically to its relaxed shape. When in its relaxed shape outwardly of the opening 94, the dumbbell shaped portion 65 is retained in place within the recessed regions 59, 61.

Figure 2:
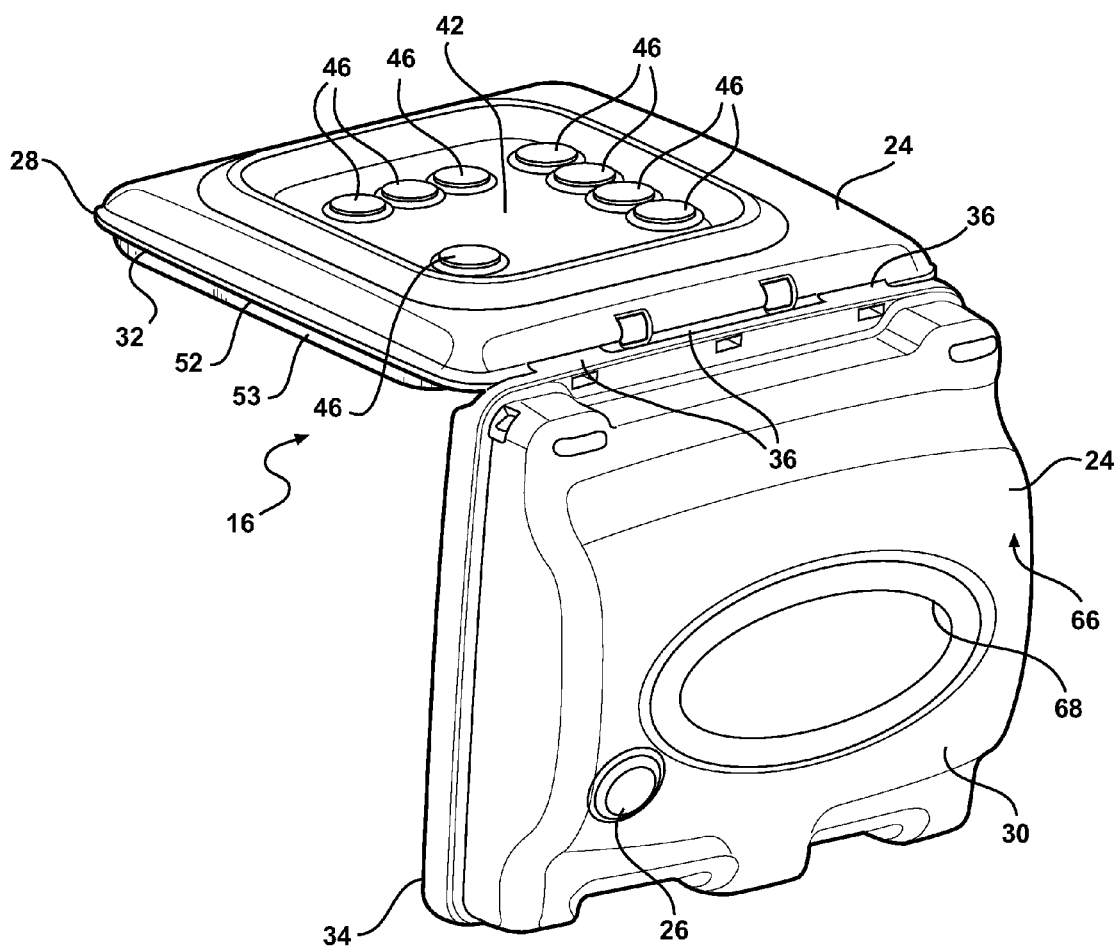
FIG. 2 is a bottom perspective view of the pump system of FIG. 1.

As shown in FIG. 2, the base 30 has a bottom surface 66 provided with a viewing window 68. The window 68 provides a clear viewing of the supply source 14 received in the cavity 18. In addition, the hydrophobic vent 26 is provided in the bottom surface 66 adjacent the window 68, by way of example and without limitation. The vent 26 can be attached to the base 30 in any suitable fashion, including being insert molded, press-fit, adhered in an opening and/or welded in an opening, for example. The vent 26 can be provided as a microporous membrane of PTFE having between about 0.2-1.0 μm sized pores, such as available from W. L. Gore, for example. As discussed, the vent 26 allows the pressure in the cavity 18 to be balanced in equilibrium with the pressure of the environment 22 by allowing the free passage of gas, while at the same time preventing fluid from passing into or out of the cavity 18. Accordingly, if the liquid drug in the supply source 14 were to inadvertently leak within the cavity 18, the liquid drug is captured in the cavity 18.

In addition to the pump 12 and the supply source 14 being received in the cavity 18, a power source 70 is received therein. The power source 70 is represented here as a standard 9-volt battery. As shown in FIG. 1, to facilitate positioning and maintaining the power source 70 in its intended location within the cavity, the cover 28 can further include a retaining or positioning tab 72. As such, upon closing the cover 28, the tab 72 is configured to engage the power source 70 to ensure it is properly positioned and to prevent it from moving within the cavity 18 during use.

Figure 6:
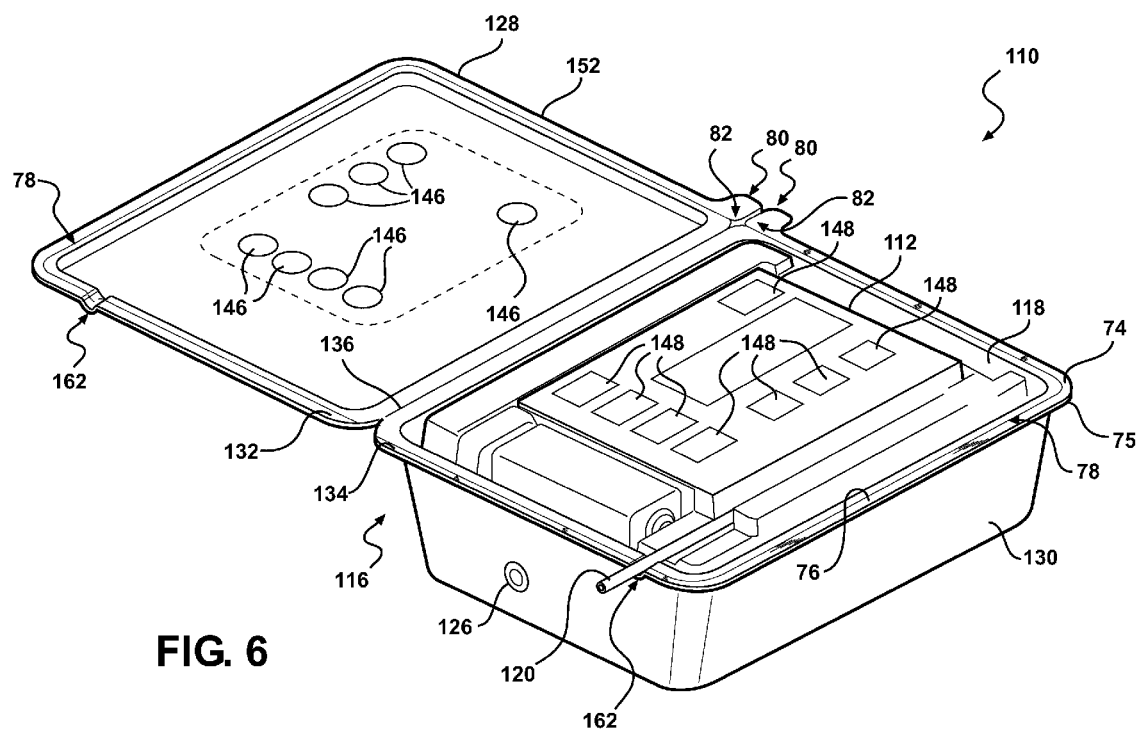
FIG. 6 a top perspective view of an ambulatory infusion pump system constructed in accordance with another presently preferred embodiment of the invention shown in an open configuration.

In FIG. 6, an assembly 110 constructed in accordance with another aspect of the invention is shown, wherein the same reference numerals, offset by a factor of 100, are used to identify like features to those discussed above. The assembly 110 includes a pump 112, a supply source (located beneath the pump 112, as shown in FIG. 5), and a housing 116. The overall function of the assembly 110 is the same as described above.

As with the assembly 10, the housing 116 has a cover 128 and a base 130 configured for liquid-tight sealed engagement with one another to prevent the passage of liquid into and out of a cavity 118 of the housing 116. The cover 128 and base 130 can be vacuum formed as a single piece of material with a living hinge 136 connecting the cover 128 to the base 130. The cover 128 and base 130 are configured to be adhered in bonded relation to one another to form the liquid-tight seal about their respective peripheries 132, 134, wherein each of the cover 128 and the base 130 are shown as having recessed U or C-shaped notches, also referred to as recesses 162, configured for operable sealed engagement about the tube 120. The notches are preferably sized for a line-to-line or slight interference fit about the tube 120 to facilitate forming a liquid tight seal thereabout. One of the cover 128 and/or base 130 has a seal, provided as an adhesive for example, such as a pressure sensitive adhesive 74, applied about its outermost periphery, and shown here as being applied about a laterally extending outermost peripheral flange 75 on the base 130. The seal adhesive 74 can also be applied to one or both of the recesses 162 to facilitate forming a liquid tight seal about the tube received therein. To allow the cover 128 and base 130 to remain open without contaminating the adhesive prior to closure, the adhesive 74 can be protected by a protective release paper 76. When a liquid-tight sealed closure is desired, the peal-away release paper 76 can be lifted from the adhesive 74, thereby exposing the seal adhesive 74, and the cover 128 can then be pivoted via the living hinge 136 into sealed and bonded abutment with the base 130 via the seal adhesive 74. The cover 128 has a laterally extending flange 152 configured to overlie and mate with the flange 75 of the base 130 in substantially mirrored relation, with the seal adhesive 74 being sandwiched between the flanges 75, 152, thereby forming a liquid-tight seal between the flanges 75, 152 and about the tube.

In order to allow access to the components within the cavity 118, the flanges 75, 152 are preferably provided with frangible features inwardly from the adhesive 74, such as a pre-scored perforation 78, about the respective peripheries 132, 134 of the flanges 75, 152. Accordingly, the frangible feature 78 is located between the seal adhesive 74 and the cavity 118. As such, after the assembly 110 has served its useful life, such as when the supply source 114 is empty, or upon desiring to service any of the internal components, the flanges 75, 152 can be separated, i.e., broken or torn away, from the remaining portion of the respective cover 128 and base 130, thereby completely removing the seal adhesive sealed joint between the cover 128 and the base 130. Accordingly, the cover 128 can be opened allowing the cavity 118 to be readily accessed and the internal components to be retrieved and reused, as desired. To facilitate breaking the respective flanges 75, 152, pull tabs 80 can be formed as integral outwardly extending pieces of the respective cover 128 and base 130 material, thereby providing ready grasping points to assist gripping and ripping the flanges 75, 152, when desired. Further, in order to facilitate initiating the ripping or breaking of the flanges 75, 152, pre-scored rip points, identified as notches 82, can be formed adjacent the tabs 80 to provide a location for tear propagation.

In contrast to the cover 28 above, rather than providing the separate control buttons 46 in the openings 44, the cover 128 can be formed as a flexible shell, thereby allowing the designated push areas or integrally formed buttons 146 to be indicated directly on the material of the cover 128. As such, the user can simply push on the marked button 146 of the cover 128, thereby causing the button portion of the cover 128 to deflect into engagement with the selected control sensor 148 on the pump 112. Of course, it is contemplated that the marked button areas on the cover 128 can be recessed or otherwise identified to assist the user in recognizing where to push on the cover 128 to attain the desire function of the pump 112.

Of course, the assembly 110 includes a hydrophobic vent 126, shown here as being incorporated into a side of the base 130, to provide the balanced pressure between the cavity 118 and the outside environment 122, and to prevent the passage of liquid between the cavity 118 and the outside environment 122.

Obviously, many modifications and variations of the present invention are possible in light of the above teachings. It is, therefore, to be understood that within the scope of the appended claims, the invention may be practiced otherwise than as specifically described.

What is claimed is:

1. An ambulatory infusion pump assembly for supplying a liquid drug and for preventing the unintended ingress and egress of liquid between an environment external to the assembly and an enclosed internal cavity of the assembly, comprising:
a housing having a cover and a base, the cover and the base connect together in a closed orientation of the housing to define the enclosed internal cavity, and the cover and the base separate from one another in an open orientation of the housing to expose the internal cavity to the external environment;
the internal cavity adapted to receive therein a container of the liquid drug to be supplied;
a tube extending from the internal cavity through the housing to the external environment;
an infusion pump within said internal cavity in fluid communication with the container and the tube within the internal cavity, the infusion pump operative to move the liquid drug from the container through the tube out of the housing;
a seal sandwiched between said cover and said base, said seal preventing fluid flow between the cover and the base when the housing is in the closed orientation; and
a hydrophobic vent in said housing, said hydrophobic vent equalizing gas pressure between said cavity and said environment and inhibiting the passage of liquid between said cavity and said environment.

2. The ambulatory infusion pump assembly of claim 1, wherein said seal includes a first portion which extends around a periphery of said cover and said base, and a second portion which engages the tube at a location where the tube extends from the internal cavity to the external environment, the second portion of the seal having a through opening extending along a central axis of the second portion between said internal cavity and said external environment, said tube being received in coaxial alignment with said central axis of said through opening and in sealed engagement with the second portion of said seal.

3. The ambulatory infusion pump assembly of claim 1, wherein the cover and the base each have surfaces which are adjacent to each other when the housing is in the closed orientation, the adjacent surfaces encircling the interior cavity when the housing is in the closed orientation, and said seal is sandwiched between and along entire lengths of both adjacent surfaces.

4. The ambulatory infusion pump assembly of claim 2, wherein the second portion of said seal extends between the cover and the base and is circumferentially discontinuous via a slit, said tube being disposed in said through opening through said slit.

5. The ambulatory infusion pump assembly of claim 4, wherein the first and second portions of said seal are portions of a single piece of elastomeric material.

6. The ambulatory infusion pump assembly of claim 2, wherein the first portion of the seal is constructed of one piece of material and the second portion of the seal is constructed of a second piece of material separate from said first piece of material, said opening being formed entirely in said second portion.

7. The ambulatory infusion pump assembly of claim 6 wherein said second portion is circumferentially discontinuous via a slit across said opening.

8. The ambulatory infusion pump assembly of claim 2 wherein said cover and said base have a laterally extending peripheral flange, said seal being disposed between said peripheral flanges.

9. An ambulatory infusion pump assembly, comprising:
a housing having a cover and a base forming an internal cavity;
a fluid pump received in said cavity in fluid communication with a supply source of liquid drug within said cavity;
a tube extending from said pump to an environment external to said cavity;
a seal sandwiched between said cover and said base, said seal forming a liquid tight seal between said cover and said base;
a vent in said housing, said vent providing an equalized gas pressure between said cavity and said environment and inhibiting the passage of liquid between said cavity and said environment; and wherein:

said seal has a through opening extending along a central axis between said cavity and said environment, said tube being received in coaxial alignment with said central axis of said through opening and in sealed engagement with said seal;

said cover and said base each have a laterally extending peripheral flange, said seal being disposed between said peripheral flanges and bonding said cover to said base; and said peripheral flanges have a pre-scored frangible feature inwardly from said seal to allow a portion of said flanges including said seal to be separated from said cover and base to allow said cavity to be readily accessed.

10. The ambulatory infusion pump assembly of claim 9 wherein said seal is provided at least in part as an adhesive.

11. The ambulatory infusion pump assembly of claim 9 wherein said flanges have generally C-shaped recesses configured in mirrored relation to one another, said C-shaped recesses providing said opening.

12. The ambulatory infusion pump assembly of claim 1, wherein said pump has at least one actuable switch and said cover has at least one resilient portion located at a position corresponding to the actuable switch to flex inwardly and outwardly into and out of engagement with said switch to activate and deactivate said switch when the housing is in the closed orientation and the resilient portion is pressed from the external environment.

13. The ambulatory infusion pump assembly of claim 12, wherein said cover is made of a first generally rigid material and said at least one resilient portion is made of a second flexible material different from said first material.

14. The ambulatory infusion pump assembly of claim 13, wherein said cover has at least one opening sized to receive therein said at least one resilient portion.

15. An ambulatory infusion pump housing, comprising:
a cover;
a base configured to mate with said cover to provide an enclosed internal cavity between said cover and said base;
a seal sandwiched between said cover and said base, said seal protecting said cavity against ingress of contamination therein and egress of liquid therefrom;
a vent in at least one of said cover and said base, said vent maintaining a substantially equalized gas pressure between said cavity and an environment external to said cavity and substantially preventing the passage of liquid between said cavity and said environment, and wherein:

said cover and said base have a laterally extending peripheral flange, said seal being disposed between said peripheral flanges and bonding said cover to said base; and said peripheral flanges have a pre-scored frangible feature inwardly from said seal to allow a portion of said flanges including said seal to be separated from said cover and base to allow said cavity to be readily accessed.

16. The ambulatory infusion pump housing of claim 15, further comprising:
an opening which extends along a central axis between said cavity and said environment, and
a tube received in coaxial alignment with said central axis of said opening.

17. The ambulatory infusion pump housing of claim 16 wherein said seal extends about a periphery of said cover and said base.

18. The ambulatory infusion pump housing of claim 16, wherein said seal extends about said tube.

19. The ambulatory infusion pump housing of claim 18, wherein said seal is circumferentially discontinuous via a slit, and said tube is disposed in said opening through said slit.

20. The ambulatory infusion pump housing of claim 19 wherein said seal is a single piece of elastomeric material.

21. The ambulatory infusion pump housing of claim 18 wherein said seal has a first portion constructed of a first piece of material and a second portion constructed of a second piece of material separate from said first piece of material, said opening through which the tube is received is formed entirely in said second portion.

22. The ambulatory infusion pump housing of claim 15 wherein said seal is provided at least in part as an adhesive.

23. The ambulatory infusion pump assembly of claim 16 wherein said flanges have generally C-shaped recesses configured in mirrored relation to one another, said C-shaped recesses providing said opening.

24. The ambulatory infusion pump housing of claim 15 wherein said cover is made of a first generally rigid material having at least one opening and further comprising a button disposed in said opening, said button constructed of a second flexible material different from said first material.

25. The ambulatory infusion pump assembly of claim 1, wherein the container of the liquid drug is pliable.

* * * * *